(12) United States Patent
Bechet et al.

(10) Patent No.: US 8,163,307 B2
(45) Date of Patent: *Apr. 24, 2012

(54) CONTROLLED RELEASE COMPOSITIONS FOR INTERFERON BASED PEGT/PBT BLOCK COPOLYMERS AND METHOD FOR PREPARATION THEREOF

(75) Inventors: Anne Chantal Bechet, Amersfoort (NL); Riemke Van Dijkhuizen-Radersma, Zeist (NL); Martin Stigter, Utrecht (NL); Jeroen Mattijs Bezemer, Utrecht (NL)

(73) Assignee: Biolex Therapeutics, Inc., Pittsboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/625,929

(22) Filed: Nov. 25, 2009

(65) Prior Publication Data

US 2010/0074868 A1 Mar. 25, 2010

Related U.S. Application Data

(63) Continuation of application No. 12/466,430, filed on May 15, 2009, which is a continuation of application No. 11/774,107, filed on Jul. 6, 2007, now Pat. No. 7,736,674, which is a continuation of application No. PCT/NL2006/000006, filed on Jan. 6, 2006.

(30) Foreign Application Priority Data

Jan. 7, 2005 (EP) ..................... 05075043

(51) Int. Cl.
*A61K 47/34* (2006.01)
*A61K 9/14* (2006.01)
*A61K 45/00* (2006.01)

(52) U.S. Cl. ............... 424/489; 424/490; 424/70.11; 424/85.4; 514/21.2

(58) Field of Classification Search ............ None
See application file for complete search history.

(56) References Cited

U.S. PATENT DOCUMENTS

| | | | |
|---|---|---|---|
| 5,192,743 A | 3/1993 | Hsu et al. |
| 5,372,808 A | 12/1994 | Blatt et al. |
| 5,611,971 A | 3/1997 | Maedera et al. |
| 5,612,052 A | 3/1997 | Shalaby |
| 5,643,605 A | 7/1997 | Cleland et al. |
| 5,711,968 A | 1/1998 | Tracy et al. |
| 5,792,477 A | 8/1998 | Rickey et al. |
| 5,980,948 A | 11/1999 | Goedemoed et al. |
| 6,110,503 A | 8/2000 | Rickey et al. |
| 6,194,006 B1 | 2/2001 | Lyons et al. |
| 6,204,308 B1 | 3/2001 | Ausborn et al. |
| 6,217,893 B1 | 4/2001 | Pellet et al. |
| 6,270,802 B1 | 8/2001 | Thanoo et al. |
| 6,291,013 B1 | 9/2001 | Gibson et al. |
| 6,294,204 B1 | 9/2001 | Rössling et al. |
| 6,379,703 B1 | 4/2002 | Lyons et al. |
| 6,440,493 B1 | 8/2002 | Gibson et al. |
| 6,465,425 B1 | 10/2002 | Tracy et al. |
| 6,471,995 B1 | 10/2002 | Ramstack |
| 6,479,065 B2 | 11/2002 | Jaworowicz et al. |
| 6,495,164 B1 | 12/2002 | Ramstack et al. |
| 6,531,154 B1 | 3/2003 | Mathiowitz et al. |
| 6,572,894 B2 | 6/2003 | Rössling et al. |
| 6,596,316 B2 | 7/2003 | Lyons et al. |
| 6,667,061 B2 | 12/2003 | Ramstack et al. |
| 6,884,372 B2 | 4/2005 | Ramstack |
| 7,265,157 B1 | 9/2007 | Igari et al. |
| 2003/0031716 A1 | 2/2003 | Tracy et al. |
| 2003/0206928 A1 | 11/2003 | Tormala et al. |
| 2004/0057996 A1 | 3/2004 | Takada et al. |
| 2004/0115277 A1 | 6/2004 | Kissel et al. |
| 2005/0019408 A1 | 1/2005 | Thumbeck et al. |
| 2005/0064039 A1 | 3/2005 | Futo et al. |
| 2005/0214330 A1 | 9/2005 | Yamamoto et al. |
| 2006/0228414 A1 | 10/2006 | Cook |
| 2007/0166352 A1 | 7/2007 | Wright et al. |

FOREIGN PATENT DOCUMENTS

| | | |
|---|---|---|
| EP | 0830859 | 3/1998 |
| EP | 0990440 | 4/2000 |
| EP | 1022020 | 7/2000 |
| EP | 1090928 | 4/2001 |
| EP | 1341522 | 6/2002 |
| EP | 1247522 | 10/2002 |
| JP | 6-145046 | 5/1994 |
| JP | H10-503198 | 3/1998 |
| JP | 2003-522156 | 7/2003 |
| RU | 2174409 | 10/2001 |

(Continued)

OTHER PUBLICATIONS

Bezemer et al., "A Controlled Release System for Proteins Based on Poly(ether ester) Block-Copolymers: Polymer Network Characterization," J. Control. Rel., vol. 62, No. 3, (1999), pp. 393-405.

(Continued)

*Primary Examiner* — Christine J Saoud
*Assistant Examiner* — Jegatheesan Seharaseyon
(74) *Attorney, Agent, or Firm* — Brinks Hofer Gilson & Lione

(57) ABSTRACT

The invention discloses a pharmaceutical composition for the controlled release of relatively toxic active compounds, in particular for bioactive proteins from the class of interferons. The composition comprises a biodegradable block copolymer constructed from poly(ethylene glycol) terephthalate (PEGT) and poly(butylene terephthalate) (PBT). The composition is provided in the form of injectable microparticles, of an injectable liquid which may have self-gelling properties, or of a solid implant. The invention further provides a pharmaceutical kit comprising the composition, methods for preparing the composition, and the pharmaceutical uses relating thereto.

8 Claims, 2 Drawing Sheets

FOREIGN PATENT DOCUMENTS

| | | |
|---|---|---|
| RU | 2191012 | 10/2002 |
| WO | WO 9321858 | 11/1993 |
| WO | WO 96/03116 | 2/1996 |
| WO | WO 9720047 | 6/1997 |
| WO | WO 9846212 | 10/1998 |
| WO | WO 00/40221 | 7/2000 |
| WO | WO 01/05380 | 1/2001 |
| WO | WO 01/58474 | 8/2001 |
| WO | WO 03035030 | 5/2003 |
| WO | WO 03041689 | 5/2003 |
| WO | WO 03051336 | 6/2003 |
| WO | WO 2006/085747 | 8/2006 |

OTHER PUBLICATIONS

Bezemer et al., "Amphiphilic Poly(ether ester amide) Multiblock Copolymers as Biodegradable Matrices for the Controlled Release of Proteins,"J. Biomed. Mater. Res., vol. 52, No. 1, (2000), pp. 8-17.
Bezemer et al., "Zero-Order Release of Lysozyme from Poly(ethylene glycol)/poly(butylenes terephtalate) Matrices," J. Conteol. Rel., vol. 64, Nos. 1-3, (2000), pp. 179-192.
Bezemer et al., "Control of Protein Delivery from Amphiphilic Poly(ether ester) Multiblock Copolymers by Varying their Water Content using Emulsification Techniques," J. Control. Rel., vol. 66, (2000), pp. 307-320.
Bezemer et al., "Microspheres for Protein Delivery Prepared from Amphiphilic Multiblock Copolymers, Part 1," J. Control. Rel., vol. 67, (2000), pp. 233-248.
Bezemer et al., "Microspheres for Protein Delivery Prepared from Amphiphilic Part 2," J. Control. Rel., vol. 67, (2000), pp. 249-260.
Crommelin et al., "Interleukins and Interferons," Pharmaceutical Biotechnology, Harwood Academic Publishers, (1997), pp. 219-222.
Hatefi et al., "Biodegradable Injectable in situ Forming Drug Delivery Systems," J. Control. Rel., vol. 80, (2002), pp. 9-28.
Kontsek et al., "The Human Interferon System: Characterization and Classification after Discovery of Novel Members," Acta Virol., vol. 47, (2003), pp. 201-215.
Mathiowitz et al., "Microencapsulation," Encyclopedia of Controlled Drug Delivery, (ed. E. Mathiowitz), John Wiley & Sons, vol. 2, (1999), pp. 493-549.
Sohier et al., "A Novel Method to Obtain Protein Release from Porous Polymer Scaffolds: Emulsion Coating," J. Control. Rel., vol. 87, Nos. 1-3, (2003), pp. 57-68.
Sohier et al., "Release of Small Water-Soluble Drugs from Multiblock Copolymer Microsheres: A Feasibility Study," Eur. J. Pharm. and Biopharm., vol. 55, No. 2, (2003), pp. 221-228.
Van De Weert et al., "Reversible Aggregation of Lysozyme in a Biodegradable Amphiphilic Multiblock copolymer," Eur. J. Pharm. and Biopharm., vol. 54, (2002), pp. 89-93.
Van Dijkhuizen-Radersma et al., "Control of Vitamin $B_{12}$ Release from Poly(ethylene glycol)poly(butylenes terephthalate) Multiblock Copolymers," Biomaterials, vol. 23, No. 6, (2002), pp. 1527-1536.
Van Dijkhuizen-RADERSMA et al., "Biocompatibility and Degradation of Poly(ether-ester)Microspheres: in vitro and in vivo Evaluation," Biomaterials, vol. 23, (2002), pp. 4719-4729.
Van Dijkhuizen-Radersma et al., "Stability Aspects of Salmon Calcitonin Entrapped in Poly(ether-ester) Sustained Release Systems," Int. J. Pharm., vol. 248, Nos. 1-2, (2004), pp. 229-237.
Van Dijkhuizen-Radersma et al., "In vitro/in vivo Correlation for $^{14}$C-Methylated Lysozyme Release from Poly(ester-ester)Microspheres," Pharm. Res., vol. 21, No. 3, (2004), pp. 484-491.
Van Dijkhuizen-Radersma et al., "Biodegradable Poly(ether-ester) Multiblock Copolymers for Controlled Release Applications: An in vivo Evaluation," J. Biomed. Mater. Res., vol. 71A, No. 1, (2004), pp. 118-127.
CN Office Action, issued in 200680007430.X.
U.S. Office Action, issued in U.S. Appl. No. 11/774,107, dated Sep. 22, 2009.
Li et al., "Clinical Application of Interferon," Mudanjiang City Hospital, 157000.
U.S. Office Action, issued in U.S. Appl. No. 12/466,430, dated Sep. 23, 2009.
RU Office Action, issued in 2007130090.
IL Office Action, issued in 184431.
Li et al., "Kinetic and Thermodynamic Modeling of the Formation of Polymeric Microspheres using Solvent Extract/Evaporation Method," J. Control. Rel., vol. 37, (1995), pp. 187-198.
Van Dijkhuizen-Radersma et al., "Biodegradable Poly(ether-ester) Multiblock Copolymers for Controlled Release Applications," 2003 Wiley Periodicals, Inc., pp. 1294-1304.
Zhou et al., "Study on Biodegradable Microspheres Containing Recombinant Interferon-α-2a," Journal of Pharmacy and Pharmacology, vol. 54, (2002), pp. 1287-1292.
Mashkovskii, Drugs, Handbook for Physicians, Moscow, Novaya Volna, S.B. Divov publisher, 2001, vol. 2, pp. 322-324.
Dawson R. et al. Biochemist's Handbook, Moscow "Mir", 1991, p. 350.
JP Office Action, issued in 2010-205413, dated Dec. 1, 2010.
RU Office Action, issued in 2007130090, Translation.
IL Office Action, issued in 184431, (2006), Summary Letter.
Han et al., "Preparation and Evaluation of Poly(L-lactic acid) Microspheres Containing rhEGF for Chronic Gastric Ulcer Healing," J. Control. Rel., vol. 75, (2001), pp. 259-269.
Khoobehi et al., "Clearance of Sodium Fluorescein Incorporated into Microspheres from the Vitreous after Intravitreal Injection," Ophthalmic Surgery, vol. 22, No. 3, (Mar. 1991), pp. 175-180.
Li et al., "Kinetic and Thermodynamic Modeling of the Formation of Polymeric Microspheres using Solvent Extract/Evaporation Method," J. Control Rel., vol. 37, (1995), pp. 187-198.
Ruiz et al., "Aggregation of Recombinant Human Interferon Alpha 2b in Solution: Technical Note," AAPS PharmSciTech, vol. 7, No. 4, Article 99, (2006), pp. E1-E5.
Chinese Office Action, issued in CN 200680007430.X, dated Aug. 5, 2011, Translation.
European Office Action, issued in EP Application No. 071220539.7, dated May 11, 2011.
European Search Report, issued in EP Application No. 10182460.5, dated May 9, 2011.
Japanese Office Action, issued in JP Application No. 2007-550316, dated Aug. 10, 2011, Translation.
Ruiz et al., "Long-Term Stabilization of Recombinant Human Interferon Alpha 2b in Aqueous Solution without Serum Albumin," International Journal of Pharmaceutics, vol. 264, (2003), pp. 57-72, EP Search Report.
European Office Action, issued in EP07120539.7, dated Mar. 9, 2009.
European Office Action, issued in EP06700417.6, dated Jan. 15, 2008.
CN Office Action, issued in 200660007430.X, Translation.
U.S. Office Action, issued U.S. Appl. No. 11/774,107, dated Sep. 22, 2009.
Li et al., "Clinical Application of Interferon," Mudanjiang City Hospital, 157000, (2001).
Li et al., "Clinical Application of Interferon," Mudanjiang City Hospital, 157000, (2001), Translation.

CONTROLLED RELEASE COMPOSITIONS FOR INTERFERON BASED PEGT/PBT BLOCK COPOLYMERS AND METHOD FOR PREPARATION THEREOF

RELATED APPLICATIONS

This application is a continuation of U.S. patent application Ser. No. 12/466,430, filed May 15, 2009; which is a continuation of Ser. No. 11/774,107, filed Jul. 6, 2007; which is a continuation of PCT application no. PCT/NL2006/000006, designating the United States and filed Jan. 6, 2006; which claims the benefit of the filing date of European application no. EP 05075043.9, filed Jan. 7, 2005; each of which is hereby incorporated herein by reference in its entirety for all purposes.

FIELD

The present invention relates to pharmaceutical compositions for the controlled release of active compounds. The compositions are in the form of polymeric microparticles, in-situ gels, or solid implants. They are based on biodegradable polymers and are particularly useful for the controlled delivery of therapeutic proteins or peptides. Moreover, the invention relates to polymeric microparticles comprised in the compositions and to methods of making such microparticles. In further aspects, the invention relates to pharmaceutical kits which comprise the compositions, and to the uses of such kits.

BACKGROUND

Parenteral dosage forms with slow drug release properties have been developed to answer the need for improving the therapeutic use of drug substances which should not be administered orally due to their physicochemical properties, and which have a relatively short half life because of which they have to be injected frequently. Frequent injections are uncomfortable to patients, and if the injections have to be given by physicians or nurses, they are also rather costly. The experience of discomfort and pain may result in patient incompliance and jeopardize the success of the therapy.

The number of drug substances which cannot be administered by the convenient oral route is presently increasing, primarily as a consequence of the recent advances of biotechnological research in the pharmaceutical area, which has lead to an increased number of highly potent peptide and protein drugs. Perhaps with the exception of some smaller peptides, however, these compounds are relatively unstable in gastrointestinal fluids and, more importantly, too large and hydrophilic as molecules to become absorbed through the intestinal mucosa to a substantial extent. For some of these drug substances, injectable or implantable controlled release formulations are being developed in order to lower the dosing frequency and thus reduce patient discomfort, and achieve a higher level of compliance and therapeutic success.

Parenteral controlled release dosage forms are usually in the form of macroscopic, solid single- or multiple-unit implants (such as polymeric rods and wafers), microparticle suspensions, and more recently also gels, including in-situ forming gels. Drug-loaded solid implants are available as non-degradable polymeric, ceramic or metal devices which have to be surgically removed after the designated period of drug action, or as biodegradable polymeric forms which require no removal. An example for a non-degradable implant is Bayer's VIADUR®, which releases the peptide drug, leuprolide, over a period of one year. An example for a biodegradable implant is AstraZeneca's ZOLADEX®, which is a polymeric rod capable of releasing the peptide drug, goserelin, over periods of one and three months, respectively.

Shortly after the market introduction of the first biodegradable implants, controlled release microparticles became available, such as Takeda's Lupron® Depot formulations, which release leuprolide over periods of one, three, and four months, respectively. In order to inject such microparticles, they have to be suspended in an aqueous carrier. For stability reasons, however, depot microparticles cannot usually be stored as an aqueous suspension, but they have to be reconstituted from a dry powder.

Various designs of drug-loaded microparticles and methods for their preparation are described in E. Mathiowitz et al., Microencapsulation, in: *Encyclopedia of Controlled Drug Delivery* (ed. E. Mathiowitz), Vol. 2, pp. 493-546, John Wiley & Sons (1999), which is incorporated herein by reference.

To enable the injection of drug delivery systems through particularly fine needles to provide increased patient comfort, drug delivery scientists have in recent years begun to develop injectable gels which are capable of forming subcutaneous or intramuscular depots. In one of the concepts, gel formulations are designed which are highly shear thinning and thixotropic. By applying shear force prior to administration, the viscosity of these gels is substantially reduced, allowing for injection with a relatively small needle, whereas the gel strength is recovered slowly after administration. According to another concept, liquid compositions are formulated which, after administration, form gels in response to changes of their environment, such as pH, temperature, ionic strength. According to a third approach, liquid polymer formulations comprising a non-aqueous solvent are injected. Upon administration, the solvent diffuses away from the injection site, which leads to the precipitation of polymeric particles or to the formation of a gel.

Biodegradable injectable gels have been discussed in detail by A. Hatefi et al., *Journal of Controlled Release* (2002) 80:9-28, which document is incorporated herein by reference.

The therapeutic usefulness of several polymeric carriers for controlled release, in particular that of polymers and copolymers of lactic acid and glycolic acid, has been demonstrated for a few active compounds, such as leuprolide, goserelin, buserelin, and triptorelin, which are all peptides with a very large therapeutic index, i.e. having a very low toxicity even at levels far above the therapeutically effective concentrations. In contrast, less tolerable active compounds such as erythropoietin and interferons, whose precisely controlled delivery is necessary for achieving therapeutic effects without intolerable side effects, have not successfully been developed as controlled release dosage forms. A major difficulty is that the biodegradable polymeric carriers used in the successful earlier product are apparently not capable of providing zero-order or nearly zero-order release profiles. Instead, they produce highly undesirable initial burst release upon administration. Furthermore, the autocatalytic degradation of polymers and copolymers of lactic acid and glycolic acid may also lead to dose dumping effects at later stages of drug release. On the other hand, other new polymers which have been discussed as improved controlled release carriers for therapeutic compounds do not have the safety record of the poly(lactides) and poly(glycolides).

Thus, there is a need for new polymeric delivery systems which have proven biocompatibility, but which are also capably of better controlling the release of relatively toxic therapeutic compounds than the previously used carriers.

It is therefore an object of the invention to provide new controlled release compositions comprising one or more polymeric carriers having excellent biocompatibility and a relatively toxic therapeutic compound which should not be given via the oral route, such as a protein.

Another object of the invention is to provide microparticles, implants, and gel compositions comprising an active compound which is released at a controlled rate. Furthermore, it is an object of the invention to provide kits which contain such compositions and pharmaceutical uses thereof. Further objects will become apparent on the basis of the following description and patent claims.

SUMMARY

The invention provides a pharmaceutical composition for the controlled release of interferons. More specifically, the composition provided by the invention comprises a biodegradable polymer and an active compound selected from the group of interferons. The biodegradable polymer is a block copolymer constructed from poly(ethylene glycol)-terephthalate (PEGT) and poly(butylene terephthalate) (PBT). A preferred active compound is an interferon selected from the family of alfa-interferons.

In a further embodiment, the composition of the invention is designed to comprise microparticles which contain the block copolymer and at least some of the interferon comprised in the composition. Such composition is particularly useful as a parenteral controlled release formulation which can be injected intramuscularly or subcutaneously.

In another embodiment, the invention provides a pharmaceutical kit comprising a first and a second sealed compartment, wherein the first compartment comprises such microparticle-based composition in substantially dry form, and wherein the second compartment comprises an aqueous liquid carrier for reconstituting the composition into an injectable microparticle suspension.

In a further embodiment, the composition of the invention is shaped as a solid implant.

Further embodiments include methods for the preparation of the composition and the pharmaceutical uses thereof.

DETAILED DESCRIPTION

Figure 1:
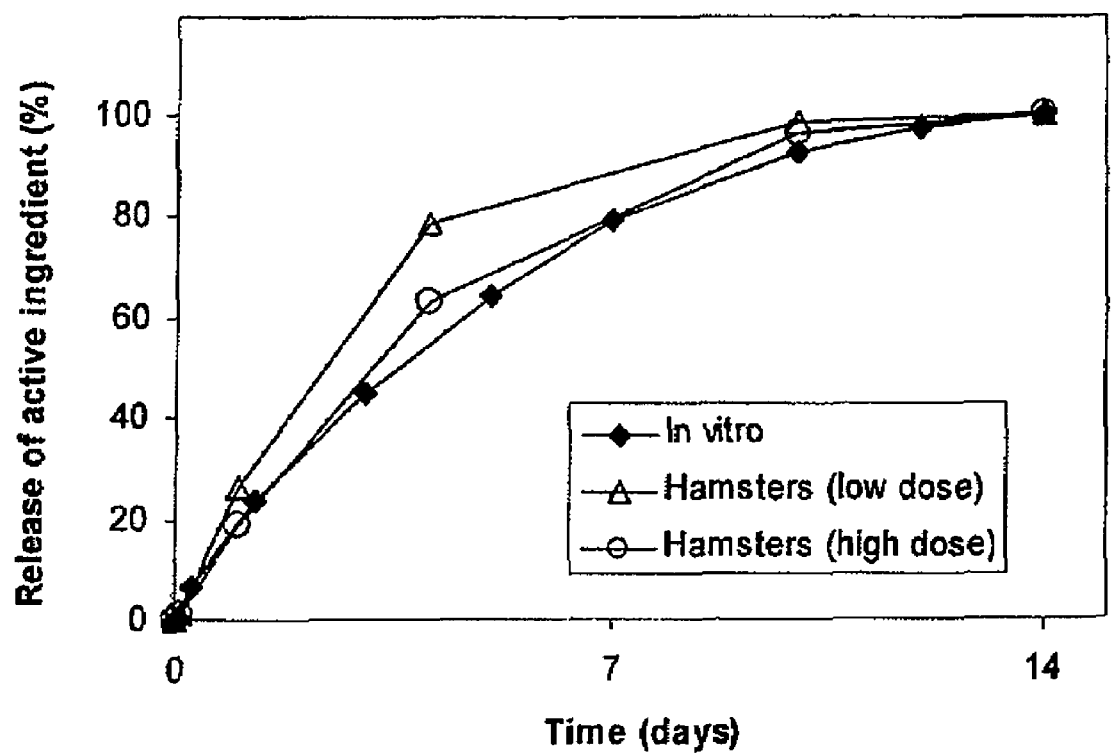
FIG. 1 represents the release of interferon from copolymer microparticles in vitro and in hamsters.
Figure 2:
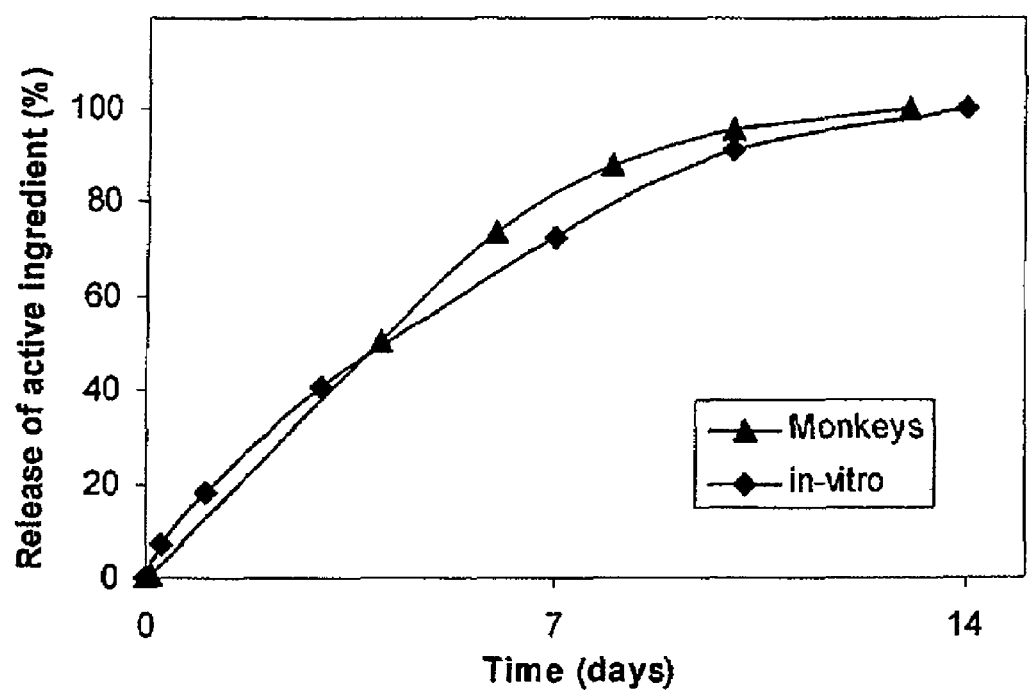
FIG. 2 represents the release of interferon from copolymer microparticles in vitro and in monkeys.

In the discovery process leading to the present invention, it has been found that many of the polymers which have been suggested as controlled release agents for active compounds, such as polymers of lactic and/or glycolic acid or, are not very suitable for the delivery of relatively toxic active compounds such as interferons. In particular, the release behavior appeared to be poorly controllable, especially when the polymers are formed as microparticles or gels. For example, it seems difficult to avoid the so-called burst release, i.e. a rapid release of a significant fraction of the incorporated active compound soon after administration, when using the conventional polymeric carriers. Depending on the therapeutic index of the respective active compound, such burst release can produce rather toxic effects in patients.

In contrast, it was surprisingly found that block copolymers of PEGT and PBT are capable of incorporating and releasing the interferons (above mentioned compounds) in a much better controlled fashion, with little or substantially absent burst effect, as will be further discussed in this description.

Therefore, the invention provides a pharmaceutical composition for controlled release comprising a biodegradable polymer and an active compound selected from the group of interferons, wherein the biodegradable polymer is a block copolymer constructed from poly(ethylene glycol)-terephthalate (PEGT) and poly(butylene terephthalate) (PBT).

It has also been found by the inventors that the block polymers described above can form a surprisingly suitable matrix for incorporating interferons for controlled release applications. In particular, they can incorporate large amounts of interferons without loss of bioactivity.

Another reason why the specified copolymers are particularly suitable is that they are able to control the release of incorporated interferons over a wide range of release profiles which may be considered desirable, depending on the specific therapeutic application. The polymeric carrier may be developed into various dosage form designs, such as microparticles, films, gels, and solid implants, and can involve a range of molecular weights and degrees of hydrophilicity which can—together with the geometry of the dosage form or a unit thereof—achieve various durations of interferon release, and various types of release profiles.

A pharmaceutical composition is defined as a composition which is typically used for therapeutic or diagnostic purposes, or for wellness and disease prevention. While many pharmaceutical compositions are designed and formulated for the immediate release of incorporated active compounds, there are also compositions which possess controlled release characteristics in order to provide an extended duration of effectiveness. Several terms have been used to describe various types of controlled release characteristics. As used herein, controlled release refers to any modified active compound release such as delayed release, prolonged release, constant or zero-order release, extended release, sustained release, slow release, biphasic release etc.

The composition comprises a biodegradable polymer. According to the IUPAC terminology, a polymer is defined as a substance composed of macromolecules. In turn, a macromolecule is a molecule of high relative molecular mass, the structure of which essentially comprises the multiple repetition of a number of constitutional units. In common language, however, the distinction between a polymer and the macromolecules which it comprises is not always made. This is also true for the present description, which may attribute features to the polymer which should—strictly speaking—be attributed to macromolecules.

Biodegradability may be defined as the ability of a substance to be chemically degraded at physiological conditions, in physiological environments, or through enzymatic action. In the context of the invention, it is preferred that the biodegradable polymer is degradable in a physiological environment—such as in physiological fluids at body temperature—even in the absence of enzymes in the sense that substantial degradation occurs within the course of hours, days, weeks, months, or years. The degradation may include various chemical mechanisms including hydrolysis or oxidation. For the avoidance of misunderstandings, biodegradability does not mean that the biodegradable polymer must degrade into the respective monomeric units. It is sufficient that the degradation process leads to soluble molecular species which can be eliminated from an organism by processes such as renal or hepatic excretion. In the present invention, the polymer typically serves as carrier for the active compound and as release controlling agent.

Furthermore, the biodegradable polymer is selected from the group of block copolymers constructed from poly(ethylene glycol) terephthalate (PEGT) and poly(butylene terephthalate) (PBT). A copolymer is defined as a polymer derived from more than one species of monomer. In a block copolymer (or block polymer), the constituent macromolecules have adjacent blocks that are constitutionally different, i.e. adjacent blocks comprise constitutional units derived from different species of monomer or from the same species of monomer but with a different composition or sequence distribution of constitutional units. A block may be defined as a portion of a macromolecule which comprises a multiple number of constitutional units that have at least one feature which is not present in the adjacent portions.

A number of block copolymers comprising PEGT and PBT have been described in prior art, for example by J. M. Bezemer et al. (*J. Control Release* 1999, 62 (3), 393-405; *J. Biomed. Mater. Res.* 2000, 52 (1), 8-17; *J. Control Release* 2000, 66 (2-3), 307-320; *Control Release* 2000, 67 (2-3), 249-260; *J. Control Release* 2000, 67 (2-3), 233-248; *J. Control Release* 2000, 64 (1-3), 179-192), R. Dijkhuizen-Radersma et al. (*Biomaterials* 2002, 23 (24), 4719-4729; *J. Biomed. Mater. Res.* 2004, 71A (1), 118; *Biomaterials* 2002, 23 (6), 1527-1536; *Pharm. Res.* 2004, 21 (3), 484-491; *Int. J. Pharm.* 2002, 248 (1-2), 229-237; *Eur. J. Pharm. Biopharm.* 2002, 54 (1), 89-93), and J. Sohier et al. (*J. Control Release* 2003, 87 (1-3), 57-68; *Eur. J. Pharm. Biopharm.* 2003, 55 (2), 221-228), and in WO 93/21858, EP 0 830 859 A2, and EP 1 090 928 A1, all of which documents are incorporated herein in their entirety.

These copolymers can be understood as being composed of repeating blocks of hydrophilic poly(ethylene glycol) (PEG) and hydrophobic poly(butylene terephthalate) (PBT). These poly(ether ester)s are typically prepared by polycondensation of PEG, butanediol and dimethyl terephthalate. Alternatively, they can be understood as being composed of repeating blocks of poly(ethylene glycol) terephthalate (PEGT) and PBT. These copolymers usually have the properties of thermoplastic elastomers. In an aqueous environment, they form hydrogels or hydrogel-like polymeric networks, in which the polymer chains are not chemically but physically crosslinked. It is believed that the crosslinking is effected by the association of "hard" PBT segments into crystalline domains, whereas amorphous regions comprising "soft" PEG segments and some PBT are responsible for the swelling behavior in water. In contrast to chemical crosslinks, these physical crosslinks are reversible at elevated temperatures or in appropriate solvents.

According to the invention, the active compound is selected from the group of interferons. Interferons represent a family of naturally occurring proteins derived from human cells and involved in various functionalities of the immune system, such as in fighting viral infections. Several interferons have been developed into pharmaceutical products and are today available as products of genetic engineering for use in the treatment of leukaemias, hepatitis, multiple sclerosis, and other severe diseases.

In contrast to several other active peptides and proteins which have been successfully developed into controlled release formulations, interferons have a relatively small therapeutic index. In other words, they show substantial toxicity at levels above the therapeutically effective concentrations. Thus, their precisely controlled delivery is necessary for achieving therapeutic effects without intolerable side effects.

One of the major classes of interferons is that of the alfa-interferons (IFN-alfa or IFN-alpha). Alfa-interferons comprise a number of native and modified proteins with similar molecular weight and functionality (see D. J. A. Crommelin et al., Pharmaceutical Biotechnology, Harwood Academic Publishers (1997), 219-222). Leukocytes are one of the major origins of these proteins in humans. At least 23 different native subtypes and several modified versions of IFN-alfa are known, some of which are available in pharmaceutical products. For example, a mixture of several native IFN-alfa subtypes derives from pooled infected human leukocytes has been commercially developed. The presently most important members of the IFN-alfa group are the recombinant variants of IFN-alfa-2a and IFN-alfa-2b. Another recombinant IFN-alfa used in therapy is IFN-alfacon-1.

The basic function of these interferons is the upregulation of the immune system, such as the stimulation of immunological cells capable of recognizing and directly or indirectly destroying cancer cells or viruses. Among the therapeutic indications for alfa-interferons are (chronic) hepatitis B, (chronic) hepatitis C, hairy cell leukaemia, (chronic) myelogenous leukaemia, multiple myeloma, follicular lymphoma, carcinoid tumor, malignant melanoma, genital warts, bladder carcinoma, cervical carcinoma, renal cell carcinoma, laryngeal papillomatosis, mycosis fungeoides, condyloma acuminata, SARS, and (AIDS-related) Kaposi's sarcoma. In fact, it is presently most preferred according to the invention that the active compound is selected from the group of alfa-interferons.

The native members of the alfa-interferons have molecular masses between 19-26 kDa and consist of proteins with lengths of 156-166 and 172 amino acids. All IFN-alpha subtypes possess a common conserved sequence region between amino acid positions 115-151 while the amino-terminal ends are variable. Many IFN-alpha subtypes differ in their sequences at only one or two positions. Naturally occurring variants also include proteins truncated by 10 amino acids at the carboxy-terminal end.

Another major class of interferons is that of beta-interferons (IFN-beta), the presently most important representatives in therapy being IFN-beta-1a and IFN-beta-1b. These interferons are used e.g. in the management of certain forms of multiple sclerosis, in particular relapsing forms of multiple sclerosis, to slow the accumulation of physical disability and decrease the frequency of clinical exacerbations. Patients with multiple sclerosis in whom efficacy has been demonstrated include patients who have experienced a first clinical episode and have MRI features consistent with multiple sclerosis.

Another therapeutically used class of interferons is that of gamma-interferons (IFN-gamma). These interferons have antiviral, antiproliferative and immunomodulatory activities. One member of the gamma-interferons, IFN-gamma-1b, is currently marketed for the management of serious infections associated with chronic granulomatous disease.

More recently, several additional classes of interferons were discovered and described, including IFN-epsilon, IFN-kappa and IFN-lambda (see P. Kontsek et al., *Acta Virol.* 2003, 47 (4):201-15).

In particular, a composition according to the invention wherein the interferon is selected from the group of alfa-interferons, and preferably from the group consisting of IFN-alfa, IFN-alfa-2a, IFN-alfa-2b, IFN-alfacon-1, pegylated IFN-alfa-2a, pegylated IFN-alfa-2b, truncated IFN-alfa-2a, truncated IFN-alfa-2b, fusion proteins of IFN-alpha and albumin, and a functional derivative thereof gives very good properties. In this context, an alfa-interferon may also represent a mixture of various alfa-interferon variants, such as a mixture of native alfa-interferons which are difficult or unnecessary to separate and purify. The interferon may be extracted from living organisms or isolated cells or cell cultures. The cells and/or organisms from which the interferon is obtained may be modified, such as by infection, in order to produce the desired interferon.

A composition according to the invention wherein the interferon is a recombinant interferon produced from genetically engineered cells or organisms, wherein the cells or organisms are preferably selected from mammalian, insect, bacteria, yeasts, fungi and higher plant cells or organisms, gives especially good properties.

One of the particularly suitable interferons for carrying out the invention is a truncated version of IFN-alfa-2b or, optionally, a mixture of more than one truncated versions of IFN-alfa-2b. For example, molecules comprising the IFN-alfa-2b amino acid sequence in which the last 5 to 10 amino acids of the N-terminus have been deleted can be prepared by the currently available methods of genetic engineering. In a further embodiment, variants of IFN-alfa-2b which are truncated by 7 or 8 N-terminal amino acids are preferred.

It is preferred that the composition of the invention exhibits a release of the active compound over a period of at least about 7 days. More preferably, the interferon is released over at least about 10 days, or at least about 14 days. In further embodiments, the release occurs over at least about 3 weeks, 4 weeks, 6 weeks, and 2 months, respectively. Presently much preferred is a release over a period of about 10 days to 1 month. Which grade of polymer should be selected and which further specific features are useful for achieving such duration of release depends at least partially on the selected dosage form design and is described in further detail below.

The invention also relates to a pharmaceutical composition for controlled release comprising a biodegradable polymer and one or more active compounds selected from the group of interferons, wherein at least about 80 wt. % of the active compound, based on the total weight of the active compound, is released in monomeric, non-aggregated form. In accordance with this embodiment of the invention, the biodegradable is preferably, but no limited to, a block copolymer as defined herein, constructed from poly(ethylene glycol) terephthalate (PEGT) and poly(butylenes terephthalate) (PBT). It has been found by the inventors that the block polymers described above can form a surprisingly suitable matrix for incorporating interferons for controlled release applications. In particular, they can incorporate large amounts of interferons without loss of bioactivity, and they appear to preserve the monomeric, non-aggregated state of the incorporated interferons. This is remarkable as interferons are known to be sensitive to various polymers and process conditions, and particularly liable to aggregation which is often associated with deactivation. In contrast, using the block polymers specified herein as carriers for interferons, it is possible to achieve that most of the incorporated interferon is released in monomeric form.

Preferably, the polymer grade and the processing conditions should be selected to ensure that at least about 80% of the incorporated active ingredient, i.e. interferon, is released in monomeric, non-aggregated form. Even more preferably, at least about 90% of the interferon is released as monomers, or according to further embodiments, at least about 95%, 97%, and 98%, respectively. These percentages are by weight, based on the total weight of the incorporated active ingredient.

Further preferred forms of the compositions according to the invention are described below.

A unit dose of the composition, which is that amount of the composition which is administered at a time, preferably comprises an amount of active compound which is equivalent to 1 million international units (MIU) of the respective interferon. The exact amount which is incorporated depends, of course, on the release profile of the composition and on the daily or weekly dose which a particular patient should receive.

In one of the embodiments, the composition is adapted to release at least about 5 MIU of interferon over 14 days, i.e. over the first 14 days after administration. In another embodiment, it comprises a dose of about 10 to about 150 MIU, which dose is released over a period of about 10 days to about 1 month, in particular over a period of about 14 days. Also preferred is a composition which comprises and releases, over the same period of time, a dose of about 20 to about 100 MIU. Such compositions are particularly preferred if the active ingredient is an alfa-interferon, such as IFN-alfa-2b or a derivative thereof.

Calculated for an average day within the period of interferon release after administration, the composition is preferably adapted to release an amount of about 0.5 to 20 MIU of the respective interferon, or from about 1 to 10 MIU. Depending on the shape of the release profile, it is possible that the amount of active ingredient released within the first day after administration is higher than 10 or 20 MIU, but the average daily release may still be in the preferred ranges.

The composition of the invention may be designed, formulated and processed so as to be suitable for a variety of therapeutic uses and modes of administration, such as topical, oral, rectal, vaginal, or ophthalmic administration; preferably, however, it is adapted for parenteral administration. As used herein, parenteral administration includes any invasive route of administration, such as subdermal, intradermal, subcutaneous, intramuscular, locoregional, intratumoral, intraperitoneal, interstitial, intralesional, with some less preference in the context of this invention also intravenous, intraarterial etc. Highly preferred routes of administration of the composition are subcutaneous and intramuscular injection or implantation.

Being suitable for parenteral administration means in particular that the composition preferably is sterile and complies with the requirements of the current pharmacopoeias with regard to the content of endotoxins, osmolality, etc. The excipients are preferably selected to be safe and tolerable for parenteral administration. In a further aspect, the composition is formulated to be relatively isotonic (or isoosmotic), such as in the region of about 150 to 500 mOsmol/kg, and preferably in the region of about 250 to 400 mOsmol/kg. Furthermore, the pH should be approximately in the physiological range in order to avoid pain and local intolerance upon injection. Preferably, the pH of the composition is in the region of about 4 to 8.5, and more preferably in the region of about 5.0 to 7.5.

The composition of the invention may be designed and formulated so as to comprise microparticles which in turn comprise the biodegradable block copolymer and the active compound, or at least a substantial fraction of the active compound present in the composition. In this case, the dosage form of the composition which is administered is typically an injectable suspension comprising the microparticles and a liquid coherent carrier.

In the context of the invention, microparticles should be understood as solid or semisolid particles having a diameter in the region of about 0.1 to about 500 μm, regardless of their shape or internal structure. For example, microparticles would also encompass microspheres and microcapsules. In a more preferred embodiment, the microparticles have a diameter from about 1 to about 300 μm. Moreover, it has been found that desirable release properties are best achieved for interferons that are incorporated into microparticles based on PEGT/PBT block copolymers which have a volume-average diameter of about 25 to about 200 μm, as measured by photon correlation spectroscopy. Selecting such particle size will also ensure that a suspension of these microparticles is well-syringeable and can be easily and conveniently administered via intramuscular or subcutaneous injection.

Within this size range, the diameter may be further optimized for specific product applications or to accommodate specific interferons. For example, in the case of—optionally truncated—interferon-alfa-2a and interferon-alfa-2b it is presently most preferred to select volume-average microparticle diameters from about 30 to about 175 μm. In further preferred embodiments, the average diameter is in the range from about 50 to about 150 μm.

Preferably, the microparticles should have a relatively low porosity. In particular, it was found that desired release profiles for controlled release applications of alfa-interferons can be best accomplished when the presence of larger pores is largely avoided. In this context, larger pores may be defined as pores having a diameter of about 5 μm or more. Thus, in one of the preferred embodiments the majority of the microparticles are substantially free of pores having a diameter of about 5 μm or more. In another embodiment, the majority of the microparticles are substantially free of pores having a diameter of about 2 μm or more.

Optionally, the microparticles may be coated with a drug-free layer of polymer. Such embodiment may be useful to prevent an initial burst release of the incorporated active compound, or even achieve a pre-determined lag-time until release begins, if so desired.

The microparticles are based on the block copolymer of PEGT and PBT, which is used as carrier and controlled release agent. It has been found, however, that not all copolymers of PEGT and PBT are equally useful to make microparticles for the controlled release of all interferons. Furthermore, the intended release time or duration of effect is important for the selection of the block copolymer. In the case of the alfa-interferons, it has been found that the copolymer should preferably comprise from about 50 to about 95 wt.-% PEGT, and consequently from about 5 to about 50 wt.-% PBT. In another embodiment, the copolymer comprises from about 70 to about 95 wt.-% PEGT. According to a yet further preferred embodiment, the copolymer contains from about 70 to about 85 wt.-% PEGT.

To further specify the chemical composition of the copolymer, the molecular weight of the PEG segments of the PEGT component is an important parameter. It has been found that alfa-interferons are very readily incorporated into copolymer microparticles whose release profile can be adjusted within useful ranges when the average molecular weight of the PEG is from about 600 to about 3,000. Even more preferably, the average molecular weight of the PEG is from about 1,000 to about 2,000.

The selection of the average molecular weight of the PEG may also take the average particle size into consideration. If, for example, a relatively small particle size is selected, e.g. for processing reasons, such as below about 100 μm, or even below about 75 μm, it is preferred to select a block polymer with a relatively low degree of hydrophilicity, i.e. having a relatively low average molecular weight of the PEG, such as about 1,500 or less, or about 1,000 or less, especially if a duration of release of two weeks or longer is desired. Alternatively, or additionally, a low degree of hydrophilicity may also be achieved by selecting a relatively low content of PEGT segments, such as not more than about 75 wt.-%.

Conversely, there may be reasons to select a relatively large average particles size, such as above about 100 μm, e.g. based on processing considerations or to achieve a desired in vivo behavior. In this case, it is presently preferred to select an average molecular weight of the PEG of about 1,000 to about 3,000, or of at least about 1,500, and/or a relatively high content of PEGT, such as at least about 75 wt.-%.

Furthermore, it may be useful to combine two or more different PEGT/PBT block copolymers for preparing microparticles having an optimized release behavior. The two or more block copolymers may differ, for example, in their relative PEGT content, or they may differ in the average molecular weight of the PEG, or they may differ in both parameters. For example, useful polymer blends for making the microparticles with alfa-interferon as active agents may comprise two polymers both having a PEGT content of about 80 wt. %, but with average PEG molecular weights of about 1,000 and about 2,000, respectively. Another useful blend comprises two polymers having a PEGT content of about 80 wt.-% and an average PEG molecular weight of about 1,000 and about 1,500, respectively. The two or more different polymers can be blended in various ratios, such as 50:50, 75:35, or 75:25.

It has been found that the compositions of the invention are suitable for incorporating alfa-interferons and achieving release times of about 1 to about 8 weeks. For example, by choosing appropriate block copolymers, the release profile may be adjusted to provide drug effects over periods from about 10 days or 2 weeks to about 4 weeks, which is the presently most preferred release time. The release time, or duration of release, should be understood as the time in which at least about 80 wt.-%, and more preferably at least 90 or 95 wt.-% of the incorporated active compound are released. The release profiles do not show any pronounced burst-effect, i.e. the initial release (within 4 hours) is not more than about 10% of the incorporated dose, and more preferably not more than about 7% of the incorporated dose.

Using the block copolymers as described above, it is possible to make microparticles incorporating therapeutically useful amounts of interferons. For example, it has been found that the polymers selected according to the preferred embodiments can incorporate alfa-interferon at a content of about 0.1 to about 20 wt. % relative to the total weight of the microparticles. More preferably, the interferon content of the microparticles is from about 0.2 to about 10 wt. %, or from 0.5 to about 5 wt. %, respectively. Within these ranges, the interferon is compatible with the polymer matrix, with little or no tendency to aggregate. At the same time, the concentration of the active substance is high enough to allow for a convenient administration of a relatively small volume of microparticle suspension which is to be injected.

Typically, the dose of alfa-interferon per injection will be in the range from about 3 to 2,400 million international units (MIU), depending on factors such as the state of the patient, the type and severity of the disease, and in particular the duration of release from the microparticles. If the microparticles are designed to release the interferon within about 2 or 4 weeks, respectively, the dose will normally be in the range from about 10 to about 150 MIU. In fact, in one of the preferred embodiments, the composition of the invention comprises interferon-alfa-2a, interferon-alfa-2b, or a fragment thereof, at a strength from about 10 to about 150 MIU per volume to be injected. According to a further preference, the composition has a strength in the range from about 20 to about 100 MIU per injection.

For the sake of patient comfort, the injection volume should not be very high, such as no more than about 3 mL in view of the preferred route of administration, which is intramuscular or subcutaneous injection. In the case of subcutaneous administration, it is more preferred that the injection volume is not more than about 2 mL. On the other hand, highly concentrated injections in very small volumes are difficult to dose precisely, for which reason it is preferred that the volume per injection is at least about 0.1 mL, and more preferably at least about 0.3 mL. The presently most preferred range is from about 0.5 mL to about 2 mL.

Even though intramuscular or subcutaneous injection of the microparticle compositions are the preferred routes of administration, it may of course be possible and useful in the case of certain patients or diseases to administer the compositions through other routes. These routes are more typically parenteral routes, but may also be the pulmonary, nasal, oromucosal—such as sublingual or buccal—or other routes. Among the useful parenteral routes besides intramuscular and subcutaneous injection are in particular intratumoral, intralesional, locoregional, arterial, interstitial, and intraperitoneal injections.

The microparticles and their suspension for injection are adapted for parenteral administration, which means that they are formulated and processed to meet the requirements of parenteral dosage forms. Such requirements are, for example, outlined in the major pharmacopoeias. In one aspect, the composition, or its premixes or the kits from which the composition is made prior to administration, must be sterile. In another aspect, the excipients must be selected to be safe and tolerable for parenteral administration. In a further aspect, the compositions are formulated to be relatively isotonic (or isoosmotic), such as in the region of about 150 to 500 mOsmol/kg, and preferably in the region of about 250 to 400 mOsmol/kg. Furthermore, the pH should be approximately in the physiological range in order to avoid pain and local intolerance upon injection. Preferably, the pH of the composition is in the region of about 4 to 8.5, and more preferably in the region of about 5.0 to 7.5.

The microparticles are usually rendered injectable by suspending them in an appropriate, physiologically acceptable liquid carrier which is preferably based on water, even though other biocompatible solvents such as ethanol, glycerol, propylene glycol, polyethylene glycol, or other organic solvents may be present. In a more preferred embodiment, the liquid constituent of the liquid carrier is aqueous and substantially free of organic solvents. On the other hand, the incorporation of other pharmaceutical excipients may be useful or needed to optimize the properties of the formulation, such as the tolerability, the performance in terms of drug release, and the stability. This may be true for both the microparticles themselves and the liquid carrier. Either phase may contain one or more additives which are physiologically tolerable.

Typically, the microparticles are resuspended in the liquid carrier to form a suspension with a solid particle content of approx. 1 to 20 wt.-%, and more preferably from about 3 to 10 wt. %. The particle size and the viscosity of the liquid vehicle are preferably selected to allow the injection with a relatively fine needle, such as with a 20 to 22 G needle. In another preferred embodiment, the particle size and the viscosity of the liquid vehicle are adapted to enable subcutaneous or intramuscular injection using a 23 to 25 G needle.

Optionally, the microparticles are designed for reconstitution using sterile isotonic sodium chloride solution for injection.

It may be useful to stabilize the interferon with a stabilizing excipient or combination of excipients, such as one or more salts, sugars, sugar alcohols, amino acids, peptides, proteins, polymers, surfactants, cryoprotectants, osmotic agents, buffer salts, acids, or bases. Some of these excipients may also be useful for other pharmaceutical reasons, such as to improve the tolerability of the microparticles or the suspension thereof. To modulate the properties of the polymeric carrier or improve its stability, it may be useful to further incorporate one or more plasticisers, pore forming agents, release-modifying agents, or antioxidants.

To avoid the agglomeration of the microparticles when suspending them in an aqueous carrier, the aqueous carrier may also contain one or more physiologically acceptable surfactants. In fact, depending on the actual presentation of the dosage form, a needed excipient such as a surfactant may be incorporated either into the aqueous carrier or into a dry composition comprising the microparticles. Selecting an appropriate surfactant may also help to ensure that the microparticles are quickly and easily reconstituted, such as in no more than about 3 minutes, or preferably within about 60 seconds, and more preferably in no more than about 30 seconds. Examples of potentially useful surfactants include poloxamers, polysorbates, phospholipids, and vitamin E-TPGS.

In a further embodiment, the invention provides a pharmaceutical kit comprising the microparticles described above. In this context, a pharmaceutical kit may be defined as a set of at least two compositions which are to be combined and used for a specific therapeutic, preventive, or diagnostic purpose. In the present case, the kit comprises a first and a second sealed compartment which may be members of the same or of two different primary packages. The first compartment comprises the composition of claim 1 in substantially dry form, whereas the second compartment comprises an aqueous liquid carrier for reconstituting this dry composition into an injectable microparticle suspension. Optionally, the kit contains two or more sets of each of the first and the second compartment.

Typically, the substantially dry composition comprised in the first compartment resembles one single dose to be injected, and usually also the second compartment will hold the volume of liquid carrier needed to reconstitute the content of the first compartment. Presently less preferred are compartments containing more than one dose to be injected at one time. It is thus preferred that the content of interferon in the first compartment is from about 10 to about 150 MIU, and that the volume of aqueous liquid carrier in the second compartment which can be removed with a needle is from about 0.3 mL to about 3 mL, in particular from about 0.5 mL to about 2 mL.

The kit further provides a secondary package which is suitable for accommodating the set or sets of first and second compartments.

The first and the second compartments may represent different chambers of a single device or a single primary package. For example, they may be the two chambers of a dual chamber syringe. The advantage of prefilled dual chamber syringes is that the preparation and administration is safe and convenient as it does not require the handling of several containers under aseptic conditions. One of the drawbacks of such syringes is that they are costly to provide, and may not always enable complete and reliable reconstitution.

Alternatively, the two compartments of a set may be members of two different primary containers or packages. For example, the first compartment comprising the substantially dry microparticle composition may be provided in the form of a sealed bottle or vial from suitable glass or plastic, and the aqueous liquid carrier may be provided in a bottle, vial, or ampoule. In a further embodiment, the first compartment is the chamber of a syringe and the second compartment is provided as a bottle, vial, or ampoule.

Optionally, one of the containers is designed as a cartridge for an auto-injecting device. Upon combining the dry composition and the aqueous liquid carrier, the ready-to-use liquid suspension is kept in the cartridge and can be loaded into the auto-injector.

Again, it should be emphasized that either the substantially dry composition in the first compartment or the aqueous liquid carrier, or both, may comprise one or more further excipients, such as fillers, bulking agents, surfactants, preservatives, acids, bases, salts, sugars, sugar alcohols, amino acids, stabilizers, antioxidants, polymers, buffers, polyols, proteins such as human serum albumin, and plasticisers.

The dry composition comprising the microparticles and the aqueous liquid carrier are adapted to yield a reconstituted suspension which is suitable for injection, i.e. which is sterile, relatively isotonic and isoosmotic, and substantially free of ingredients which are toxic when administered parenterally. The viscosity should be low enough to allow injection with a needle of 17 gauge or higher, and more preferably with a needle of 20 gauge or higher, or even with a needle of 22 gauge. As used herein, the capability of being administered refers to rheological properties which allow the injection with the specified needle type without requiring an injection force of more than about 25 N. More preferably, the rheological properties are adapted, and a needle size selected, to enable injection with a force of no more than about 20 N, and even more preferably with an injection force of no more than about 15 N, to allow the administration also to be performed by physicians, nurses, or patients who are not particularly sinewy. Of course, another prerequisite for such needle sizes is that the diameter of the microparticles is sufficiently small, and the microparticles do not aggregate after reconstitution. As mentioned above, the weight average diameter of the majority of microparticles should not be higher than about 200 µm, and more preferably be in the range of about 30 to about 175 µm.

The microparticles of the invention may be prepared by any method known to produce microparticles from amphiphilic polymers, such as by spray drying, coacervation, acoustic droplet formation followed by de-solvatation, spray freeze drying etc. More preferably, however, the microparticles are produced by an emulsion-based method which includes the steps of (a) preparing an emulsion comprising an aqueous inner phase comprising the active ingredient, and an organic outer phase comprising the biodegradable polymer and at least one organic solvent; (b) solidifying the biodegradable polymer into microparticles by removing at least a fraction of the organic solvent from the emulsion prepared in step (a), and (c) collecting and drying the microparticles formed in step (b). The basic process design is described e.g. by J M. Bezemer et al. in J. Control Release 2000, 67 (2-3), 233-248 and 249-260, and J. Control Release 2000, 66 (2-3), 307-320, the disclosure of which is incorporated herein by reference.

Generally speaking, the microparticles are formed from an organic polymer solution which is dispersed as droplets in an aqueous or hydrophilic phase. In order to solidify into particles, the organic solvent must be at least partially removed from the dispersed phase. This can be accomplished by a step of solvent extraction or solvent evaporation, or a combination of both. Solvent extraction means that the continuous aqueous phase is modified to such extent that it is capable of dissolving or extracting a substantial part of the organic solvent of the dispersed phase. For example, if the organic solvent has some moderate water miscibility, a dilution or volume increase of the aqueous phase may already effect some substantial extraction of the organic phase. Alternatively, the composition of the outer phase may be modified by adding one or more organic solvents which are miscible with water, but which can act as cosolvents to dissolve and extract the organic solvent of the dispersed phase. For example, ethanol, methanol, acetone, isopropyl alcohol may be used as such cosolvents.

Solvent evaporation, on the other hand, does not require the addition of any components to directly influence the composition and properties of the organic phase, but makes use of the typically much higher vapor pressure of the organic solvent of the dispersed phase in comparison to that of the aqueous phase: by applying a vacuum and or heat, the organic solvent may be evaporated. Upon reaching a certain polymer concentration in the organic phase, the polymer solidifies and microparticles are formed. It is important to note that any solvent evaporation of the dispersed phase will usually include the presence of the mechanism of solvent extraction as well.

In order to incorporate hydrophilic active compounds into the microparticles, it may not be advisable to charge the organic phase with the active ingredient directly. Firstly, this may lead to poor incorporation efficiency as hydrophilic compounds will partition into the aqueous phase when the emulsion is formed. Secondly, many compounds of interest, especially peptides and proteins such as the interferons which are to be incorporated according to the present invention, are rather sensitive to organic solvents and may become inactivated. It is therefore preferred that the interferon is incorporated in form of an aqueous solution which is emulsified into an organic solution of the block copolymer to form a "water-in-oil" emulsion, which is subsequently emulsified into another aqueous phase to form a "water-in-oil-in-water" (w/o/w) double emulsion. When carrying out the solvent extraction or solvent evaporation step as described above, the inner aqueous phase comprising the interferon becomes encapsulated into the polymeric microparticles.

One of the presently preferred organic solvents to dissolve the block copolymer and to provide the organic phase of the o/w-emulsion or w/o/w-double emulsion is dichloromethane. The polymer content of the organic phase may vary according to the specific polymer composition and the organic solvent(s) which are actually used, and may range from about 1 to about 300 mg/mL. More preferably, the polymer content should be in the range from about 50 to about 250 mg/mL, or even from about 100 to about 150 mg/mL in the case that dichloromethane is used as solvent.

The active ingredient, i.e. the interferon, is preferably incorporated in the form of an aqueous solution which is emulsified into the organic polymer solution. The aqueous interferon solution may be stabilized by excipients, such as by acids, bases, or buffer salts to achieve and maintain a certain pH value, or by osmotic agents such as one or more salts, sugars, sugar alcohols, amino acids etc. Some of these excipients may also be valuable for stabilizing effects other than related to osmolality. However, it has been found that interferon, and in particular the alfa-interferons, can be readily incorporated using the w/o/w-double emulsion technique using a simple aqueous interferon solution as innermost emulsion phase which contains no further excipients.

The interferon content of the inner aqueous phase will obviously influence the interferon content of the microparticles, and may therefore be selected according to the desired microparticle properties. In the case of the alfa-interferons, for example, the content may range from about 1 to about 100 mg/mL, and more preferably from about 10 to about 50 mg/mL.

The ratio of the volume of the inner aqueous phase to that of the organic phase will also have an impact on the content of active ingredient of the microparticles. Furthermore, it may influence other important properties of the particles such as their porosity and release profile. Therefore, the ratio should be carefully adjusted to the desired product characteristics in each individual case. If the features of the inner aqueous and the organic phases are selected according to the preferences discussed above, a volume ratio of about 1:3 to about 1:15 (inner aqueous phase:organic phase) has been found useful. According to one of the preferred embodiments, the volume ratio is selected from about 1:5 to about 1:10.

To stabilize the w/o/w-double emulsion, it may be useful to incorporate one or more stabilizers having surfactant properties into the outer aqueous phase. Useful stabilizers may be small amphiphilic molecules such as ionic or nonionic surfactants or detergents, or surface-active polymers. For example, it has been found that polyvinyl alcohol is a useful additive capable of stabilizing the emulsion without having any substantial detrimental effects on the preparation method or on the final product. Useful polyvinyl alcohols may have an average molecular weight ranging from about 10,000 to about 1 million, and have a degree of hydrolysis from about 80 to about 99%, and more preferably from about 85 to about 90%. Alternatively, polyvinyl pyrrolidone or surface-active polysaccharides may be used. The content of the stabilizer in the outer phase depends on its chemical nature, as well as on the nature and relative volume of the dispersed organic phase. In the case of polyvinyl alcohols, for example, it may range from about 0.1 to about 10 wt.-%, and more preferably from about 0.5 to about 5 wt.-%. In the case of polyvinyl pyrrolidone, the useful ranges are from about 1 to about 30 wt.-%, and more preferably from about 5 to about 25 wt.-%.

The outer aqueous phase may also contain further excipients, such as buffering agents, osmotic agents, or cosolvents. Cosolvents such as ethanol or methanol may be used to modulate the hydrophilicity of the aqueous phase and improve any solvent extraction step of the preparation process. Osmotic agents may, for example, be selected from the group of salts, sugars, sugar alcohols, oligosaccharides, glycols, other alcohols, and amino acids. In one of the preferred embodiments, sodium chloride is used as an osmotic agent. It should be noted that also any buffer system present in the outer phase will induce some osmotic pressure.

It may be useful to adjust the osmolality of the outer phase to a value which is equal to, or higher than, that of the innermost aqueous phase of the double emulsion. In this way, the osmotically driven diffusion of water from the outer aqueous phase to the inner aqueous phase may be largely avoided. It has been found that such diffusion process may increase the porosity of the microparticle formed by solvent extraction and/or solvent evaporation in a subsequent step. More preferably, the osmolality of the outer aqueous phase is adjusted to substantially exceed that of the innermost aqueous phase, such as by incorporating sodium chloride at a level of about 3 to about 6 wt.-%

The relative volume of the outer phase must be selected above the minimal volume needed for the incorporation of the two other phases, and thus depends also on the nature and composition of all phases, in particular of the organic phase and the outer aqueous phase. Above the minimal volume, the actual volume of the aqueous outer phase is important primarily in view of the subsequent solvent extraction and/or solvent evaporation process. Usually, the volume of the outer aqueous phase is larger than that of the w/o-emulsion to be incorporated therein. For example, it may be at least twice as large as the volume of the w/o-emulsion. More preferably, it is about 5 to about 40 or 50 times as large.

The preparation of the inner w/o-emulsion may be carried out using conventional high-shear equipment, such as high-speed rotor-stator devices, e.g. of the Ultra-Turrax type, if the active ingredient is relatively stable to shear force. To emulsify such emulsion in an aqueous phase comprising a surface-active compound, it may not be needed to apply high shear or agitation: conventional stirring equipment may be sufficient. The preparation of the w/o- and w/o/w emulsions is preferably conducted at room temperature, or at temperatures below room temperature, such as between about 0° C. and about 25° C., and at normal pressure. Obviously, the emulsification method used with influence the resulting average diameter and distribution of the dispersed phase, and the size and size distribution of the microparticles. Other factors to influence these parameters are the compositions of the respective phases, an in particular the nature of the organic solvent and the type and content of the surface-active stabilizer in the outer phase.

The solidification of the polymer dissolved in the organic phase to form microparticles may be induced by solvent evaporation as primary mechanism. This can be accomplished by increasing the temperature of the w/o/w-double emulsion under stirring, and/or by applying a vacuum.

More preferably, however, the microparticle formation is induced by a step which includes solvent extraction. To do this, the outer phase of the w/o/w-double emulsion is diluted with additional aqueous solution which may, optionally, be similar or even identical in its composition to that of the outer aqueous phase. If the stabilizer content of the outer aqueous emulsion phase is sufficiently high, the aqueous solution which is added for inducing the solvent extraction process may not need to contain any further stabilizer. On the other hand, it is recommended that the aqueous solution which is added contains an osmotically active ingredient, such as one or more salts, sugars, sugar alcohols, oligosaccharides, glycols, other alcohols, and amino acids, in order to maintain any osmotic gradient between the inner and outer aqueous phases of the double emulsion, and to avoid water diffusion into the inner phase. Optionally, the aqueous solution to be added may also contain a cosolvent such as methanol or ethanol, or a buffering agent.

The volume of the aqueous solution which is added to the double emulsion is typically at least as large as that of the emulsion before conducting the solvent extraction step. More preferably, the volume is from about 1 to 5 times that of the double emulsion. It may be advisable to add the solution slowly under constant stirring to avoid local inhomogeneity within the vessel. Optionally, the temperature may be elevated and/or some vacuum applied to remove some of the extracted organic solvent. After the addition of the aqueous solution, stirring may be continued for some time to allow for a more extensive solvent extraction from the organic phase, and perhaps also to enable the diffusion of water from the inner aqueous phase of the emulsion to the outer phase.

After the microparticles are solidified, they may be collected, such as by centrifugation, filtration, or sieving. Repeated centrifugation, filtration, or sieving after resuspending the microparticles in some fresh aqueous solution such as buffer should be conducted to remove substantially all remaining organic solvents and all soluble compounds whose presence in the microparticles is not desired. Optionally, the microparticles may be screened to separate a desired particle size fraction.

After washing, the microparticles may be dried for storage. A preferred drying method is freeze drying. For example, the microparticles may be frozen in liquid nitrogen and subsequently dried under vacuum to sublime the residual water. Usually, the drying process comprises a first drying phase which is conducted under temperatures below 0° C. followed by a secondary drying phase at ambient or even higher temperatures.

The dried microparticles may be mixed with further optional excipients as described above to arrive at the composition of the invention. For example, a powder mixture comprising the microparticles and one or more solid-state excipients selected from the group of surfactants, resuspending agents, osmotic agents, and buffering agents may represent the composition according to claim 1. Preferably, the microparticles and the excipients are provided in sterile form, and the mixing is conducted aseptically. Such powder mixture may be aseptically filled into bottles or vials. As mentioned above, the bottles or vials may be combined with an aqueous liquid carrier for reconstituting the powder with pharmaceutical kits.

In a further embodiment, the composition of the invention is provided in the form of an injectable liquid formulation. In this embodiment, the interferon and the block copolymer are dissolved or dispersed in a liquid carrier which should be physiologically acceptable. Upon parenteral administration, the polymer solution or dispersion will form a depot in the muscle or subcutaneous tissue from which the interferon is slowly released. This embodiment is based on the discovery that the block copolymers of the composition of the invention are indeed capable of forming macroscopic gels in a physiological environment.

Preferably, the liquid formulation is composed and adapted to be capable of forming a gel after injection. A gel may be defined by virtue of its rheological properties. As used herein, a gel is a semisolid material which behaves like a solid upon the exertion of low shear force, and like a viscous fluid when the shear force exceeds a threshold which is defined as the yield point. In other words, a gel is a system with a finite, usually rather small, yield stress.

Injectable gels and in-situ-forming gels as controlled release dosage forms have been described by A. Hatefi et al., J. Control. Rel. 80 (2002), 9-28, which document is incorporated herein by reference. There are several general approaches to the formulation of an injectable gel, most of which are based on the use of gel-forming polymeric carriers. For example, certain polymers may form gels which are responsive to certain conditions of the environment, such as pH or temperature. For example, sol-gel systems have been described which are present as sols (viscous, colloidal liquid solutions) at a relatively low pH or at room temperature. When injected, the pH is slowly buffered by physiological fluids to a more neutral value, resulting in solidification and gel formation. In a temperature-responsive system, the temperature rises after injection to a physiological level, leading to the gelling of the system.

More preferably, however, the injectable solution comprises a non-aqueous, biocompatible organic solvent, or cosolvent, which in vitro provides a liquid solution or suspension, but which, after injection, slowly diffuses away from the block copolymer, which is insoluble but capable of gel formation in an aqueous environment.

The organic solvent or cosolvent may be selected from those organic solvents which are capable of dissolving the block copolymer(s) and which may be considered biocompatible in view of the intended administration volume and frequency. Examples of such solvents include benzyl alcohol, benzyl benzoate, diacetin, tributyrin, triethyl citrate, tributyl citrate, acetyl triethyl citrate, acetyl tributyl citrate, triethylglycerides, triethyl phosphate, diethyl phthalate, diethyl tartrate, polybutene, glycerine, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decylmethylsulfoxide, oleic acid, 1-dodecylazacycloheptan-2-one, and mixtures thereof.

In one of the preferred embodiments, the non-aqueous solvent is one or more members of the group consisting of DMSO, NMP, benzyl alcohol, tetrahydrofuran, ethyl acetate, and benzyl benzoate.

The block copolymer content of the liquid injectable composition is typically from about 5 wt.-% to about 60 wt.-%, primarily depending on the precise polymer or polymers which are actually used. More preferably, the polymer content is from about 15 to about 45 wt.-%.

Particularly suitable block copolymers for carrying out this aspect of the invention comprise a relatively high average PEGT content, such as from about 70 to about 98 wt.-%, and more preferably from about 75 to about 95 wt.-%. Presently most preferred are block copolymers having an average PEGT content from about 80 to about 90 wt.-%.

The average molecular weight of the PEG segments of the PEGT blocks is typically from about 300 to about 6,000, and more preferably from about 600 to about 2,000.

Optionally, the composition may comprise more two or more one block copolymers which differ in their PEGT content, in the molecular weight of the PEG segments, or in both of these parameters. In a preferred embodiment, the composition comprises one or two block copolymers.

Again, the composition may comprise one or more further excipients, such as one or more cosolvents, surfactants, preservatives, acids, bases, salts, sugars, sugar alcohols, amino acids, stabilizers, antioxidants, osmotic agents, and polymers. The rationale for incorporating any of these excipients may be the same as discussed further above in the context of microparticle-based compositions. Alternatively, an excipient may serve any function typically associated with liquid injectable formulations.

Typically, the volume of the liquid formulation is from about 0.3 to about 3 mL per dose to be injected, and more preferably from about 0.5 to about 2 mL.

The injectable formulation of the invention is typically designed for intramuscular or subcutaneous injection. These routes of administration necessitate certain quality-related properties which are generally required for parenteral products, such as sterility. Thus, it is preferred that the injectable liquid formulation is sterile and meets all requirements of parenteral dosage forms as specified in the major pharmacopoeias, such as the current United States Pharmacopoeia (USP).

The injectable liquid formulation can be prepared by dissolving the block copolymer(s) the in the non-aqueous biocompatible solvent, optionally at an elevated temperature. The active compound, i.e. the interferon, may be added to this polymer solution as a dry powder, such as a lyophilized powder, under stirring. Preferably, the interferon is not incorporated in form of an aqueous solution in order to avoid the presence of water in the formulation.

As a further embodiment, the invention provides the composition of claim 1 in form of a macroscopic solid implant. An implant may be defined as a solid, substantially dry dosage form which is different from microparticles in that an implant typically contains a single dose of active ingredient within a single dosage unit, or within only a few units. Usually, the largest dimension of an implant is in the range of several millimeters or more, whereas microparticles are administered as multiple units and have dimension below the millimeter scale.

In one of the preferred embodiments, the implant is shaped as a rod. This is particularly advantageous in terms of a "less invasive" administration which largely avoids tissue injury. Furthermore, polymeric rod-shaped articles may be prepared efficiently by melt extrusion followed by cutting the extrudate into rods. To carry out such extrusion, the block copolymer(s), the interferon, and the further excipients should be provided in dry powder or granule form and mixed homogeneously. Subsequently, the mixture is fed into an extruder, such as a single or twin screw extruder, and extruded into a coherent solid strand which is then cut into individual rods.

The composition of the block copolymer may be selected as discussed in the context of the microparticles further above. A type of excipient which may be particularly useful in implants is a plasticizer, which may decrease the melting range or glass transition point of the polymer(s) to temperature which does not have a negative impact on the stability of the incorporated interferon. Potentially useful plasticizers include glycerol, propylene glycol, and polyethylene glycol.

Irrespective of whether the composition is provided in the form of a microparticle-based formulation, an injectable liquid or gel, or a solid implant, the pharmaceutical use is the preparation of a drug product for the management of diseases and conditions which may be treated, or whose progression may be prevented or decelerated, by the administration of an interferon, and most preferably by the administration of an alfa-interferon. Examples of these diseases and conditions include acute and chronic hepatitis B, acute and chronic hepatitis C, hairy cell leukaemia, acute and chronic myelogenous leukaemia, multiple myeloma, follicular lymphoma, carcinoid tumor, malignant melanoma, condyloma acuminata, SARS, and Kaposi's sarcoma, such as AIDS-related Kaposi's sarcoma.

The composition of the invention provides the advantage over conventional interferon formulations for injection that the frequency of injection may be greatly reduced by virtue of its controlled release characteristics, such as to one injection every 2 or 4 weeks instead of several injections per week. As a consequence, patient comfort and compliance are increased, and the costs associated with frequent injections potentially reduced. With regard to other polymeric controlled release systems for injection or implantation, the present invention provides excellent compatibility with interferons, improved release control without burst effect, dose dumping, or autocatalytic polymer degradation and erosion. Furthermore, the delivery systems of the invention are physiologically well-tolerated, without producing any significant carrier-related side effects.

Without wishing to be bound by a particular theory, the good release behavior of the delivery systems of the invention seems to be related to the fact that the active compound is released primarily through diffusion, and not through erosion as in the case of many of the presently known poly(lactide)- and/or -(glycolide)-based delivery systems. Using amphiphilic block copolymers, there is no autocatalytic polymer degradation involved in the release process. In contrast to the known delivery systems, the block copolymers do not produce an acidic microenvironment which is hostile to sensitive biological compounds. On the other hand, the hydrophilic blocks of the block copolymers probably provide a hydrophilic microenvironment which enhances the in-situ stability of such sensitive biological compounds. In particular, it seems that interferons—especially interferons of the alpha family—are stabilized in a non-aggregated state in the microenvironment provided by the amphiphilic block copolymers in the carrier systems of the invention.

Especially in the case of microparticles, it is also believed that the relatively low porosity of the particles formed from the block copolymers is one of the causes of the low burst effect observed in the compositions of the invention.

Further embodiments, applications and advantages of the invention will become obvious from the following non-limiting examples, or may be easily derived by persons skilled in the field of drug delivery on the basis of this description.

Example 1

Preparation of a W/O/W Double Emulsion Containing Interferon-Alfa-2b

Non-glycosylated, recombinant interferon-alfa-2b (IFN-$\alpha$-2b), a protein composed of 165 amino acids, having a molecular weight of approx. 19,000 Da and an isoelectric point of about 6.0, was obtained in form of an aqueous solution with a protein concentration of approx. 10 mg/mL. Block copolymer of 80 wt.-% PEGT and 20 wt.-% PBT with PEG segments having an average molecular weight of 1,500 was obtained from IsoTis, Bilthoven, The Netherlands. A solution of 1 g polymer in 7 mL of dichloromethane was prepared. To prepare a w/o-emulsion, 1 mL of the IFN-alfa-2b solution was added to the polymer solution under stirring, followed by ultra turrax homogenization at 19,000 rpm for approx. 30 seconds.

Two different w/o/w-double emulsions were prepared by pouring two w/o-emulsions—prepared as described above—separately into 50 mL of (a) an aqueous PBS buffer containing 4% PVA (w/v) (MW approx. 130,000, degree of hydrolysis approx. 87%), or (b) an aqueous sodium chloride solution (5% w/v) also containing 4% PVA (w/v) under stirring at 700 rpm.

Example 2

Preparation of Microparticles by Solvent Extraction and Evaporation

The double emulsions prepared according to Example 1 were further processed to prepare microparticles. To each of the two double emulsions, 100 mL of aqueous PBS buffer was slowly added under continuous stirring at 700 rpm. The added PBS solution led to an expansion of the outer aqueous phase of the double emulsions. Subsequently, stirring was continued for approx. 1 hour to extract the major part of the dichloromethane into the outer aqueous phase, and to the solidification of the polymer in the organic phase. Subsequently, the solidified microparticles were centrifuged at 2,500 rpm and at room temperature. The supernatant was discarded, and the pellet was resuspended in fresh PBS buffer to be centrifuged again. The procedure was repeated three times. Finally, the microparticles were frozen in liquid nitrogen and freeze dried over approx. 12-24 hours. The encapsulation efficiency was determined to be about 85% for the microparticles from the w/o/w double emulsion whose outer phase contained 5% sodium chloride, and approx. 25% for the other batch. The microparticles were examined by electron microscopy (SEM) and found to be roughly spherical and predominantly in the size range of about 50 to about 120 µm.

Example 3

Interferon-Alfa-2b Release from Microparticles In Vitro

For testing their release behavior, approx. 15 mg of each batch of the microparticles prepared according to Example 2 were weighed in 1.5 mL flasks in triplicate. To each flask, 1 mL of PBS buffer was added. The flasks were kept in a water bath at 37° C. At sampling times, the microparticles were centrifuged at 1,000 rpm for 2 minutes at room temperature. Samples of 700 µl were withdrawn and replaced by fresh PBS buffer. The amount of IFN-alfa-2b in each sample was determined with a Micro bichinchonic acid total protein assay.

It was found that both batches clearly demonstrated sustained release characteristics. The batch obtained from the w/o/w double emulsion whose outer phase contained 5% sodium chloride showed an initial burst effect of less than about 10%, while the other batch had a burst effect of about 20%. Both batches released 50% of their interferon content within about 3-4 days, and 75% within about 7-8 days. After 14 days, approx. 85-90% of the incorporated dose was released.

Example 4

Preparation of a Composition Comprising Microparticles Incorporating Truncated IFN-Alpha-2b A microparticle-comprising composition was prepared as follows, using aseptic conditions. A quantity of 6 g of a sterile block copolymer of 77 wt.-% PEGT and 23 wt.-% PBT with PEG segments having an average molecular weight of 1,500 was weighed and dissolved in 54 g sterile dichloromethane. The organic polymer solution was combined with 5.5 mL of a sterile aqueous solution comprising a mixture of N-terminally truncated INF-alpha-2b molecules having, in average, a length of about 158 amino acid residues, a specific activity of about 0.25 to 0.35 MIU per μg, and an interferon concentration of about 10 mg/mL. An ultraturrax device was used to obtain a homogenous water-in-oil emulsion.

Subsequently, the emulsion was combined under stirring with 445 g of a sterile aqueous solution of polyvinyl alcohol (4% w/v) which also contained sodium chloride (5% w/v). Thereby, a w/o/w double emulsion was obtained in which the polyvinyl alcohol solution formed the outer aqueous phase.

In the next step, microparticles were formed and hardened by the removal of solvent from the organic phase, which was accomplished by a combination of solvent extraction and solvent evaporation. Some solvent extraction was conducted by the addition of sterile PBS buffer to the continuous phase of the double emulsion, and another portion of dichloromethane was evaporated by blowing sterile nitrogen at a flow rate of about 5-10 L/min over the surface of the double emulsion for about 24 hours.

The microparticles were collected and washed with sterile mannitol solution (26.7 g/L) and resuspended in an appropriate volume of mannitol solution to adjust the osmolality to a physiologically tolerable value and to enable adequate cake formation upon lyophilization. Aliquots of the suspension were filled into sterile glass vials and freeze dried, resulting in white lyophilisates. The vials were closed with plastic stoppers and aluminum caps.

Analytical testing showed that the number average diameter of the microparticles was about 83 μm, and from the interferon content it was concluded that the encapsulation efficiency was higher than about 90%. The residual dichloromethane was substantially below 600 ppm. Electron micrographs of the microparticles revealed little porosity; in particular, most of the particles had no pores having a diameter of more than about 2-5 μm.

Example 5

In Vivo Testing of Microparticles Comprising a Truncated IFN-Alpha-2b

Microparticle-comprising compositions prepared in analogy to example 4 were tested for their in vivo performance in hamsters and monkeys. The solid lyophilized compositions were suspended in a sterile aqueous solution of sodium carboxymethyl cellulose (0.1% w/v), optionally further containing mannitol to adjust the osmolality of the liquid phase. The amounts of aqueous solution were calculated, based on the content of active ingredient and the dose to be administered, to yield injection volumes of 0.5 to 1.0 mL per single administration. Each of ten hamsters received a dose of 0.99 mg/kg of the active compound administered by s.c. injection every 7 days, and another group of ten hamsters received 3.46 mg/kg every 7 days. Serum samples were obtained from the animals at selected intervals, which samples were stored in frozen form and later analyzed for their interferon content. All animals appeared to tolerated the treatment well.

Based on the serum profiles, the in vivo release profiles of the active compound were calculated. In a separate experiment, the in vitro release profiles were determined as described in Example 3. A comparison of the in vivo and in vitro release profiles showed that there was a good correlation between the respective profiles, both in shape and in duration of release, and that the in vitro release behavior appears to be an excellent predictor of the in vivo performance of the compositions. There was no significant burst effect in vivo or in vitro.

FIG. 1 shows the calculated average in vivo release profiles of the low dose hamster group, the high dose group, and the respective in vitro release profile, normalized to 100% total release.

In another series of experiments, samples of the same composition were administered subcutaneously to male and female monkeys. The dose of active ingredient was 180 μg per animal, and the same reconstitution liquid was used to disperse the composition to a volume of 0.5 to 1.0 ml per injection. Starting from the time of injection, serum samples were obtained at selected time intervals over a period of 14 days. Again, the serum concentrations were used to calculate the in vivo release profiles, which were then compared to the in vitro release profiles determined from other samples of the same batch of the composition according to the method described in Example 3.

In result, the correlation between the respective release profiles was remarkable. Both in vitro and in vivo the composition appeared to release its interferon content steadily over a period of 14 days, without any substantial burst release.

FIG. 2 shows the calculated average in vivo release profile and the respective in vitro release profile, normalized to 100% total release.

Example 6

Purity of Released Interferon

Samples of the released interferon obtained from in vitro release testing as described in Examples 4 and 5 were analyzed by high-performance size-exclusion chromatography to determine the fraction of interferon which was release in monomeric form. Remarkably, it was found that less than 1% of the release active compound was in the form of dimers or larger aggregates, even though alpha-interferons are known to agglomerate easily. Thus, the microparticle composition has apparently contributed to substantial stabilization of the interferon.

Example 7

Preparation of Film Composition Incorporating Block Copolymer and Interferon-Beta A quantity of 0.5 g of a block copolymer of 80 wt.-% PEGT and 20 wt.-% PBT with PEG segments having an average molecular weight of 2,000 was weighed and dissolved in 3.5 mL dichloromethane. 1.94 mg of lyophilized interferon-beta were dispersed in the solution using an ultraturrax. The dispersion was cast onto glass plates, using an adjustable film applicator. After evaporation of the dichloromethane, films were obtained and stripped from the glass plate. The films were dried further in the fume hood for some hours.

Samples of about 1.77 cm$^2$ were cut out from the films and incubated in an aqueous acetate buffer solution pH 3.5 (1 ml) at 37° C. in a shaking water bath. After every 24 hours of incubation, the whole volume of release medium was refreshed and the samples were further incubated. Aliquots of the withdrawn buffer were used for HP-SEC analysis, which revealed that about 83% of the incorporated beta-interferon was released in monomeric, non-aggregated form. The duration of release depended on the thickness of the films.

Example 8

Preparation and Release Properties of Self-Gelling Block Copolymer Solution Containing IFN-Alfa-2a Interferon-alfa-2a and a PEGT/PBT block copolymer containing 85 wt.-% PEGT with PEG segments having an average molecular mass of about 1,000 were obtained in dry form. The polymer was dissolved in a mixture of benzyl benzoate and benzyl alcohol (98:2) at a concentration of 20 wt.-%. The interferon was added in powder form at a concentration of 4 wt.-% and thoroughly mixed with the polymer solution. The resulting mixture was filled into a syringe with a needle and injected into PBS buffer solution at 37° C. Upon injection, an irregular gel slowly precipitated. The gel was kept at 37° C. under continuous agitation. Samples were withdrawn at appropriate time intervals and replaced by fresh PBS buffer solution. The samples were analyzed for their content of IFN-alfa-2b and confirmed a release time of more than about 14 days (90% release).

The invention claimed is:

1. A method for the preparation of a pharmaceutical composition comprising microparticles including one or more active compounds selected from the group of interferons and one or more biodegradable block copolymers constructed from poly(ethylene glycol) terephthalate (PEGT) and poly (butylene terephthalate) (PBT), wherein the average molecular weight of the polyethylene glycol (PEG) is from about 1,000 to about 2,000 daltons, wherein the block copolymer comprises from about 50 to about 95 wt.% PEGT, and wherein the composition comprises a dose of at least 20 MIU of interferon that is released over a period of about 10 days to about 1 month, comprising the steps of:
   (a) preparing an emulsion comprising
      (aa) an aqueous inner phase comprising the one or more active compounds, and
      (ab) an organic outer phase comprising the one or more biodegradable block copolymer and at least one organic solvent;
   (b) solidifying the one or more biodegradable block copolymer into microparticles by removing at least a fraction of the organic solvent from the emulsion prepared in step (a);
   (c) collecting and drying the microparticles formed in step (b) wherein step (b) is carried out by emulsifying the emulsion prepared in step (a) in a coherent aqueous phase to obtain a w/o/w-double emulsion, wherein the coherent aqueous phase comprises an osmotic agent, wherein the osmolality of the coherent aqueous phase is higher than that of the aqueous inner phase.

2. The method of claim 1, wherein the osmotic agent is a salt.

3. The method of claim 2, wherein the salt is sodium chloride.

4. The method of claim 3, wherein the sodium chloride is present at a level of about 3 to about 6 wt. %.

5. The method of claim 1, wherein the interferon is selected from the group of alpha-interferons.

6. The method of claim 2, wherein the interferon is selected from the group of alpha-interferons.

7. The method of claim 3, wherein the interferon is selected from the group of alpha-interferons.

8. The method of claim 4, wherein the interferon is selected from the group of alpha-interferons.

* * * * *